(12) United States Patent
Ulman et al.

(10) Patent No.: US 12,004,901 B2
(45) Date of Patent: Jun. 11, 2024

(54) IDENTIFYING AN OPTIMAL IMAGE FROM A NUMBER OF ULTRASOUND IMAGES

(71) Applicant: KONINKLIJKE PHILIPS N.V., Eindhoven (NL)

(72) Inventors: Shrutin Ulman, Bangalore (IN); Navaneetha Krishnan Santhana Naidu, Bangalore (IN); Girish Krishnamurthy, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 735 days.

(21) Appl. No.: 17/257,656

(22) PCT Filed: Jul. 5, 2019

(86) PCT No.: PCT/EP2019/068167
§ 371 (c)(1),
(2) Date: Jan. 4, 2021

(87) PCT Pub. No.: WO2020/008063
PCT Pub. Date: Jan. 9, 2020

(65) Prior Publication Data
US 2021/0267570 A1    Sep. 2, 2021

(30) Foreign Application Priority Data

Jul. 6, 2018 (EP) .................................... 18182191

(51) Int. Cl.
*A61B 8/08* (2006.01)
*A61B 8/00* (2006.01)
(Continued)

(52) U.S. Cl.
CPC .......... *A61B 8/0866* (2013.01); *A61B 8/4236* (2013.01); *A61B 8/5292* (2013.01);
(Continued)

(58) Field of Classification Search
CPC ... A61B 8/0866; A61B 8/5292; A61B 8/5223; A61B 8/5246; G06T 2207/10132; G06T 2207/30044; G06T 7/0012
See application file for complete search history.

(56) References Cited

U.S. PATENT DOCUMENTS

2006/0100521 A1    5/2006  Takeuchi
2010/0217123 A1    8/2010  Eran et al.
(Continued)

FOREIGN PATENT DOCUMENTS

WO    2017196030 A1    11/2017

OTHER PUBLICATIONS

International Search Report and Written Opinion for International Application No. PCT/EP2019/068167, filed Jul. 5, 2019, 12 pages.

*Primary Examiner* — Boniface N Nganga

(57) ABSTRACT

The invention relates to a method of identifying, from a number of ultrasound images (34) acquired during an ultrasound examination of a subject (6), the ultrasound image best suited to analyze a pre-determined anatomical structure of the subject. The method comprises the steps of (a) Providing a number of ultrasound images (34) acquired during an ultrasound examination of the subject; (b) Deriving at least one biometric parameter (96) related to the anatomical structure from a physical examination of the subject, (c) Retrieving a reference image (38) showing a target view of the anatomical structure (35); (d) For each of the number of ultrasound images (34), calculating an image similarity index between the ultrasound image and the reference image, (e) For at least the ultrasound image(s) having the best image similarity index, determining (100) a biometric parameter from the ultrasound image, and calculating a biometric similarity index, i.e. a measure of the agreement between the biometric parameter, as determined from the ultrasound image, and the corresponding biometric (Continued)

parameter as derived from the physical examination; and (f) selecting the optimal ultrasound image based on the biometric similarity index, and optionally on the image similarity index.

14 Claims, 5 Drawing Sheets

(51) Int. Cl.
*G06T 5/40* (2006.01)
*G06T 7/00* (2017.01)
*G16H 30/20* (2018.01)
*G16H 50/30* (2018.01)

(52) U.S. Cl.
CPC .............. *G06T 5/40* (2013.01); *G06T 7/0014* (2013.01); *G16H 30/20* (2018.01); *G16H 50/30* (2018.01); *G06T 2207/10132* (2013.01); *G06T 2207/30044* (2013.01)

(56) References Cited

U.S. PATENT DOCUMENTS

| | | |
|---|---|---|
| 2011/0196235 A1 | 8/2011 | Dunbar et al. |
| 2012/0232394 A1 | 9/2012 | Toji |
| 2014/0200449 A1 | 7/2014 | Yoo et al. |
| 2017/0007208 A1 | 1/2017 | Deng et al. |
| 2017/0360412 A1 | 12/2017 | Rothberg et al. |
| 2017/0367685 A1 | 12/2017 | Zou et al. |
| 2019/0183460 A1 | 6/2019 | Ryu et al. |

IDENTIFYING AN OPTIMAL IMAGE FROM A NUMBER OF ULTRASOUND IMAGES

RELATED APPLICATIONS

This application is the U.S. National Phase application under 35 U.S.C. § 371 of International Application No. PCT/EP2019/068167, filed on Jul. 5, 2019, which claims priority to and the benefit of European Application No. 18182191.9, filed Jul. 6, 2018, which are incorporated by reference in their entireties.

FIELD OF THE INVENTION

The invention relates to a method of identifying, from a number of ultrasound images acquired during an ultrasound examination of a subject, the ultrasound image best suited to analyze a pre-determined anatomical structure of the subject. The invention further relates to a computer program, a computer-readable medium as well as a system configured to assist an operator of an ultrasound system in obtaining an ultrasound image well-suited to analyze a pre-determined anatomical structure of a subject.

BACKGROUND OF THE INVENTION

Ultrasonography has become a widespread medical imaging modality, since the cost of the equipment is moderate compared to other medical imaging modalities. However, correct interpretation of ultrasound images requires trained healthcare workers, which are not available everywhere. A major limitation of the ultrasound imaging modality is related to its operator dependency, having a fairly steep curve to competency.

In particular, obstetric ultrasonography is considered an integral part of prenatal care, as it has been shown to accurately date a pregnancy, identify pregnancy risk factors, and diagnose foetal abnormalities. Recently, there has been an increase in utilization of obstetric ultrasound in limited-resource settings around the world with the goal of identifying high-risk pregnancies and directing their care to hospital settings that are able to manage pregnancy complications. However, such increased utilization of ultrasound, in particular obstetric ultrasound, is limited by the lack of trained operators of the ultrasound imaging modality. In the field of obstetrics, foetal movement and variable foetal position in the uterus further affect ultrasound imaging.

US 2017/0360412 A1 discloses a method for guiding an operator to use an ultrasound device, whereby operators with little experience in operating ultrasound devices may capture medically relevant ultrasound images. The method is based on analyzing an acquired ultrasound image using a deep-learning technique, and providing instructions to the operator to move the ultrasound device.

US 2011/0196235 A1 discloses an ultrasound imaging system, comprising an ultrasound scanner, as well as an assistance means for providing at least one demonstration video clip and at least one video display. The video display is configured to present the demonstration video clip simultaneously with a live ultrasound image. According to an embodiment, the video display may further show animated ultrasound images that result or would result from performing the procedural step as demonstrated in the demonstration video clip.

US 2006/0100521 discloses an ultrasonic diagnostic apparatus comprising a navigation information generating unit, configured to provide a user with navigation information, helping the user to acquire an ultrasonic image at a position corresponding to that of a reference image. A navigation processor is configured to find similarities between the currently picked-up ultrasound image and the reference image, for example through image processing, or image recognition.

US 2012/232394 A1 discloses an ultrasound diagnostic apparatus configured for: generating three-dimensional data for each region in the body of a subject based on ultrasound waves reflecting back from the body of the subject; selecting, for each region, one of the two-dimensional cross-sections that compose the three-dimensional data, as a measurement reference image used for measuring a length of each region; measuring a length of each region using the respectively selected measurement reference image; calculating an estimated weight of the subject using the measured lengths; and outputting the estimated weight thus calculated.

OBJECT OF THE INVENTION

It is an object of the present invention to provide a method, a related computer program and a system allowing an operator of an ultrasound system to obtain an ultrasound image well-suited to analyze a pre-determined anatomical structure of a subject. Further, it is an object of the invention to provide a tool for improving image quality and reducing measurement error of an ultrasound scan, in particular an obstetric ultrasound scan.

SUMMARY OF THE INVENTION

To better address one or more of the above-identified concerns, according to a first aspect of the invention, a method of identifying the ultrasound image best suited to analyze a pre-determined anatomical structure, from a number of ultrasound images acquired during an ultrasound examination, is presented in claim 1. According to further aspects of the invention, a computer program, a computer-readable medium and a system configured to assist an operator of an ultrasound system are provided. Useful embodiments are set out in the dependent claims and further described herein. Any features, embodiments and advantages disclosed with regard to one aspect or claim category of the invention is also applicable and may be embodied in any other aspect and claim category.

In accordance with the first aspect, there is provided a method of identifying, from a number of ultrasound images acquired during an ultrasound examination of a subject, the ultrasound image best suited to analyze a pre-determined anatomical structure of the subject, the method comprising the steps of providing a number of ultrasound images acquired during an ultrasound examination of the subject;
  providing at least one biometric parameter related to the anatomical structure, the biometric parameter being derived from a physical examination of the subject, and/or from the subject's medical history;
  retrieving a reference image from a database, the reference image showing a target view of the anatomical structure;
  for each of the number of ultrasound images, calculating an image similarity index between the ultrasound image and the reference image;
  for at least the ultrasound image(s) having an image similarity index above a certain threshold, or having the best image similarity index, determining a biometric parameter from the ultrasound image, and calculating a biometric similarity index, which is a measure of the agreement between the biometric parameter, as determined from the ultrasound image, and the corresponding biometric parameter as derived from the physical examination and/or the subject's medical history;

based on the biometric similarity index, and optionally on the image similarity index, selecting an ultrasound image as being best suited to analyze the anatomical structure.

The method compares a number of ultrasound images, preferably a series of currently picked-up or "live"-images, to a reference image, and calculates an image similarity index therefrom, which may guide the operator towards the optimal image. Preferably, the ultrasound images are the "live" images of the anatomy just being scanned, and the reference image is a model for the final image to be obtained before taking measurements on the anatomical structure. In addition, the invention advantageously compares at least one biometric parameter related to the anatomical structure, as obtained from an ultrasound image, to the corresponding biometric parameter as derived from a physical examination or from the subject's or patient's medical history. The degree of agreement between the biometric parameter determined by these two means is reflected in a biometric similarity index, which may then be used to identify an ultrasound image from a number of images as being best suited to analyze the anatomical structure. The use of biometric parameters and the use of a physical examination to obtain comparison values for such biometric parameters will improve the reliability of the match between the reference image and an acquired ultrasound image. A further advantage of the invention is that clinically appropriate referrals may be made, since the biometry measurements have fewer errors.

The subject is usually a human subject or patient, e.g. a pregnant lady. The number of ultrasound images is preferably a series of live-images, i.e. an ultrasound image which has just been acquired by an operator from the subject. The method is preferably carried out in real-time, i.e. the similarity indices described herein are preferably calculated within e.g. 1-50 ms after the corresponding live image has been acquired, so as to avoid measurable delay between the presentation of the live image and the corresponding similarity indices.

In obstetric ultrasound, the pre-determined anatomical structure is preferably the uterus or a foetus, and wherein the operator may desire to perform one of the six steps detailed by the International Society of Ultrasound in Obstetrics and Gynaecology (ISUOG). Based on the step selected, or any other diagnostic question, a reference image is retrieved from a database, the reference image showing a target view of the anatomical structure. Thus, the reference image is usually a real ultrasound image acquired previously from another subject, and showing the anatomical structure in an exemplary way. The reference image is preferably stored in a database, together with labels or metadata allowing a suitable reference image to be retrieved for every anatomical structure and diagnostic question, e.g. the database may hold reference images for any organ of the body such as the heart, lungs, thyroid, brain, kidneys, ovaries, uterus and pregnancies in various gestational ages.

The ultrasound images will usually be B-mode images, but may also be Doppler-images. They are usually two-dimensional images acquired by moving an ultrasound (US) probe over the body surface of the subject, or by using an US catheter or transoesophageal US probe. In case of obstetric ultrasound, the ultrasound images are usually acquired by moving the probe over the abdomen of the pregnant lady, wherein the field of view captured by the probe is determined by probe position and angulation. However, the invention is also applicable to three-dimensional ultrasound images.

The method further provides a step of providing at least one biometric parameter derived from a physical examination of the subject, preferably performed prior to the ultrasound examination, although the biometric parameter may also be obtained from the subject's medical history. A biometric parameter is any parameter, which can be measured from the body, or derived from at least one parameter which is directly measured in a physical examination of the subject, i.e. any metric related to human characteristics. Thus, the biometric parameter may e.g. be the length, circumference or weight of an anatomical structure or the subject. It may also be a (secondary) biometric parameter, which is derived or calculated from another (primary) biometric parameter directly obtained from the subject, such as a body-mass index (BMI), which is calculated from the size and weight of the subject. In obstetric applications, the at least one biometric parameter is for example foetal weight, foetal head circumference, foetal length, gestational age (GA) etc. According to an embodiment, the biometric parameter is a secondary biometric parameter derived or calculated from a primary biometric parameter obtained from a physical examination of the pregnant subject, such as her size, weight, weight gain during pregnancy, abdominal girth, or symphysiofundal height. In obstetrics, it is usual that the pregnant woman is subjected to a physical examination before ultrasound scanning, so these biometric parameters will naturally be available to the operator. Thus, the operator may preferably enter the at least one primary biometric parameter derived from the physical examination into the system before commencing the ultrasound scan, and if necessary the method may comprise a further step of deriving at least one secondary biometric parameter related to the anatomical structure from the at least one primary biometric parameter obtained from the physical examination of the subject.

Examples for suitable (primary or secondary) biometric parameters are the expected volume of an organ, such as the liver, the lung or the heart, and which may be estimated based on parameters such as the subject's weight, abdominal girth, heart rate and medical history. The biometric parameter may further be the expected length, shape, circumference or width of an organ or anatomical structure. In obstetrics, a suitable biometric parameter is the foetal weight, which may be derived from the symphysiofundal height in accordance with Johnson's formula. However, foetal weight may also be estimated based of abdominal girth of the pregnant lady, the assumed GA and possibly other parameters.

In a next step, a reference image is retrieved from a database. The database may be local, but may be available over a remote connection, e.g. over the internet. Thus the database may be stored on a PC, network of computers, cloud computer, server, or other data storage medium.

The reference image is used, preferably during the ultrasound scan, for calculating an image similarity index between the currently acquired image and the reference image. Preferably, such similarity index will be calculated for each acquired ultrasound image but it may also be calculated only for a selection therefrom, to save calculation time. The image similarity index is calculated by comparing the live image with the reference image, preferably based on the presence or absence of characteristic or relevant features. In useful embodiments, such comparison is purely image-based, i.e. relying only on the image content. The value of the image similarity index may be displayed continuously in a graphic representation such as a number or color, thereby aiding the operator to adjust the position and the angle of the probe to obtain the ultrasound image best suited to analyze the anatomical structure (also referred to as optimal image). In useful embodiments, the image similarity index has a value between 0 (no similarity) and 1 (maximum similarity), but other scales are possible.

The number of ultrasound images acquired during the ultrasound examination, such as the live images, are stored in useful embodiments, e.g. on a storage medium connected to a processor carrying out the inventive method. In such embodiment, the similarity indices may be calculated and the optimal image identified retrospectively. Alternatively, the method may be conducted entirely in real-time, wherein similarities indices are calculated immediately and images (and corresponding similarity indices) are immediately overwritten. Most preferred, the similarities indices are calculated in real-time, but are saved together with the respective images.

The inventive method further includes a step of determining a biometric parameter from at least the ultrasound image(s), having an image similarity index above a certain threshold, or having the best image similarity index, and calculating a biometric similarity index, which is a measure of the agreement of the biometric parameter as calculated from the ultrasound image and the corresponding biometric parameter as derived from the physical examination. Accordingly, the estimated biometric parameter derived from the physical examination is matched with the corresponding biometric parameter determined from an ultrasound image, preferably from an image having a high image similarity index, i.e. the biometric similarity index may act as a confirmation of the selection of optimum image made through the image similarity index. Such biometric similarity index may be determined for each of the number of ultrasound images but may be limited to those ultrasound images having a reasonably good image similarity index, i.e. above a certain threshold. Alternatively, or if no image is above the threshold, those images having the best similarity index may be used for determining the biometric parameter. In useful embodiments, the biometric similarity index has a value between 0 (no similarity) and 1 (maximum similarity), but other scales are possible.

Based on the biometric similarity index and optionally on the image similarity index, the optimal ultrasound image is selected. The selection may be made manually, e.g. by the operator, but while or after he has checked the biometric similarity index and/or the image similarity index. Alternatively, the selection may be made automatically, e.g. the image with the best biometric similarity index is selected, or the image having the best overall similarity, as determined by more than one similarity index. For example, the biometric similarity index may be combined with further similarity indices to give a matching index as explained below, and the image with the best matching index is selected. The selection may also be semi-automatic, i.e. the images having the best similarity indices are presented to the user, and he picks one of them for further analysis. In a further embodiment, only the image with the best image similarity index is used for determination of the biometric similarity index, and if the latter is above a certain threshold, that image is selected as the image best suited for analysis.

Accordingly, the invention is unique in using the patient's physical examination data. Thus, the optimal image selected for analyzing the anatomical structure is always guided by the physical examination of the subject, and this reduces error and improves scanning efficiency.

A useful example of such biometric parameter is the foetal weight, which may be derived from a physical examination of the pregnant lady by means of Johnson's formula, and may—for comparison—be determined from an ultrasound image of the foetus, for example by measuring head circumference, abdominal girth of the foetus and femoral length. These parameters may be used to estimate the foetal weight by Hadlock's formula or by any other formula devised for a certain population. In a preferred embodiment, the foetal weight obtained via sonography is compared to that obtained using Johnson's formula. A good match of e.g. within +/−250 g between the two values is a confirmation of the optimal image. This is performed over and above the image similarity index, thereby improving reliability. Alternatively, the foetal weight may also be estimated from the gestational age obtained from the patient's medical history, including information provided by the pregnant lady.

According to a preferred embodiment, the reference image is selected from a number of reference images of the anatomical structure, based on at least one biometric parameter derived from the physical examination of the subject and/or from the subject's medical history. Accordingly, also the reference image is preferably chosen using the patient physical examination data. This improves the quality of the reference image, since it will be more similar to the live images obtained from the subject. Accordingly, an image quality index close to what is achievable in a given patient is achieved, making the target view of the ultrasound scan personalized. This increases safety and reduces error as well as scan time. Again, useful (primary or secondary) biometric parameters derived from the physical examination of the subject and/or the subject's medical history may be his or her size, weight, BMI etc. In case of obstetric ultrasound, the selection of the reference image is preferably based on the known gestational age (GA), but possibly also the weight of the pregnant lady, BMI, weight gain during pregnancy, abdominal girth etc. Further biometric parameters derived from the subject's medical history may be demographic parameters like the subject's age, population, etc. In a useful embodiment, the database will contain a separate reference image e.g. for each or every second week of GA, with possible further choice of reference images depending on further biometric parameters like BMI.

According to a preferred embodiment, the subject is a pregnant woman and the anatomical structure includes a foetus. As explained above, in obstetric ultrasound, where the anatomical structure (i.e. the foetus) changes rapidly with gestational age, it is particularly useful to provide a tool to the operator which uses a personalized reference image, and which includes biometric parameters derived from physical examination of the pregnant lady, in order to confirm a similarity between a live ultrasound image and the reference image.

In a preferred embodiment, the biometric parameter is the estimated foetal weight, which may be derived from a physical examination using Johnson's formula in the following manner: For the measurement of the symphophysiofundal height the woman is asked to empty her bladder, and then asked to lie in supine position with legs extended. The fundus is defined by placing the ulnar border of the left hand against the upper border of the uterus. One end of a non-elastic tape is placed on the upper border on the pubic symphysis, and gently stretched over the midline of the abdomen up to the above-mentioned position of the ulnar border of the left hand. Thus, the fundal height is measured in centimetres. When such measurements were taken in 100 women in each category at 24, 28, 32, 36 and 40 weeks of gestation, a normogram was constructed from the reading. The mean, standard deviation, tenth percentile, $50^{th}$ percentile and $90^{th}$ percentile of the fundal height measurements was taken to determine its relationship to gestational age. Foetal weight is calculated by the below Johnson's formula for measurement for foetal weight in vertex presentation as:

$$\text{Foetal weight (g)} = (\text{Symphysiofundal height in cm} - X) \times 155$$

Where

X=13, when the presenting part is not engaged, i.e. the anatomical part of the foetus which is leading, has not yet lowered into the pelvis X=12, when the presenting part is at 0 station;

X=11, when the presenting part is at +1 station.

If the patient weighs more than 91 kg, 1 cm is subtracted from the fundal height.

Thereby, by a simple measurement of fundal height, a useful estimate for the foetal weight may be gained. For the ultrasound image, a corresponding estimate for foetal weight can be obtained by measuring head circumference, abdominal girth and femoral length. These parameters are used to estimate the foetal weight by Hadlock's formula, or by any other formula. Preferably, the head circumference, abdominal girth and femoral length are automatically determined, although it is also possible that such biometric parameters are determined by the operator making the measurements. In this case, such measurements will be made on only one or a few of the ultrasound images having a good image similarity index.

According to a further useful embodiment, the image similarity index between an ultrasound image, preferably a live image and a reference image is calculated by one or more of the following steps:

identifying and comparing characteristic features, in particular anatomical features or geometric features, of the ultrasound image and the reference image;

computing and comparing grey level histograms of pixel values of the ultrasound image and the reference image.

Thus, the image similarity index is preferably purely a measure of the similarities between the two images to be compared. Preferably, the image similarity index is calculated quickly and efficiently, wherein the identification of characteristic features, such as used in feature tracking methods, has been found reliable. For example, the method will match the anatomies seen on the two images, wherein characteristic features may be e.g. lips, neck, abdomen, limbs of a foetus etc. The image similarity index is then computed based on the degree of agreement in these characteristic features between the two images, in particular whether they are present or absent in both. It may be possible to look for characteristic features depending on the pre-determined anatomical structure, but preferably the method uses an algorithm which is not expecting any particular features to be present in the images. Preferably, the image similarity index is not calculated by means of a trained neural network, e.g. a deep learning algorithm. This increases the speed of scanning, since such image similarity index may be calculated in real-time, i.e. within 1-50 ms of acquiring a live ultrasound image.

The image similarity index may further be calculated by using grey-level histograms. Thereby, the number of pixels having a grey-level within certain ranges is calculated within a certain field of view, which may be the whole image, but may also be a part of it, in order to analyze only the region of interest. Such region of interest may for example include the anatomical structure and may be derived by image segmentation techniques. The grey-level histograms thus obtained from the ultrasound image and the reference image may be quickly compared, and a degree of similarity may be calculated. The similarity index may be calculated using one or both above-described steps, i.e. (1) matching characteristic features and (2) comparing grey-level histograms. The image similarity index may then be a weighted average of the two. In useful embodiments, the degree of similarity in either case is given as a value between 0 (no similarity) and 1 (maximum similarity), although any other scale is also possible.

Preferably, the biometric similarity index is calculated by automatically or manually taking measurements on the anatomical structure on at least the ultrasound image(s) having an image similarity index above a certain threshold, or having the best image similarity index, and calculating the biometric similarity index therefrom. For example, a length, width or circumference of the anatomical structure, e.g. the foetus or a limb, head or abdomen therefrom, may be measured. This can be done automatically, but can also be done manually or semi-automatically by displaying the image and the user placing cursors on suitable landmarks on the image. Usually, the biometric parameter is related to the distance between such cursors, and can then be calculated automatically.

According to useful embodiments, the method uses further tools for comparing the ultrasound image to the reference image, as detailed below:

In a useful embodiment, the method comprises a step of, for at least one of the number of ultrasound images, automatically fitting a pre-determined curve or geometrical shape to an anatomical structure shown in the ultrasound image, and determining the coefficients of the fitted geometrical shape or curve.

Accordingly, the similarity between live image and reference image may be further determined using geometric similarities, in particular the equations of curves or geometrical shapes, automatically drawn onto the two images. For example, the method will identify characteristic anatomical structures visible in the image, e.g. water-filled cavities like the amniotic sack, the bladder, the ventricles of the brain or other cavities. The anatomical structure may be any organ, such as the stomach bubble or the liver, the heart, or a part of a foetus, e.g. the foetus head, abdomen, a limb etc. Once the outline of such anatomical features have roughly been determined, for example by means of a segmentation or other method, a suitable geometric shape or curve will be fitted thereto. A suitable geometrical shape includes a line, an ellipse, an oval, a circle, or a polygonal shape, or a more elaborate shape being adapted for example to the ventricles of the brain. A suitable curve includes a polynomial function or a spline function, which may be fitted for example to a prominent blood vessel or the circumference of an organ. This is done on the ultrasound image and on the reference image, wherein, of course, the curves or geometrical shapes may be fitted to the reference image beforehand, so that the reference image is retrieved together with metadata including the coefficients of the fitted curve or geometrical shape. Once the curve or geometrical shape has been fitted to the anatomical structure of the ultrasound image, the coefficients of the fitted geometrical shape or curve are determined. For example, such coefficient may be the diameter of a circle, the length of the minor and major axis of an ellipse or oval, the length or degree of curvature of a line, and of course the constants of a polynomial or spline function. In the fitting, preferably the curve or geometrical shape is distorted such that it will still have the same form and degree but will not be defined by the same coefficients and constants.

According to a useful embodiment, the coefficients of the fitted curve or geometrical shape are used to derive a biometric parameter, to be compared with the corresponding biometric parameter derived from the physical examination and/or the subject's medical history. For example, the crown-rump length (CRL) of the embryo or foetus may be used to derive an estimate of gestational age. Thus, CRL is useful biometric parameter, which can be determined from the ultrasound image by fitting a suitable line or other curve or geometrical shape to the foetus, and may be compared to the CRL which follows from the GA given by the pregnant woman, i.e. available from her medical history. Further useful biometric parameters are the biparietal diameter (BPD) or head circumference (HC), which are also good predictors or gestational age. Further useful biometric parameters are the abdominal circumference (AC), and the femur length (FL), which is a measurement of the upper thigh bone, the longest bone in the body. Typically, measurements for HC, BPD, AC and FL are entered into a mathematical formula, such as Hadlock's formula or Shepherd's formula, to estimate the foetal weight. Accordingly, the biometric parameter may be selected from HC, BPD, AC, FL or foetal weight, and may be compared with corresponding parameters derived from physical examination and/or the subject's medical history, e.g. the foetal weight as derived by Johnson's formula described above. Alternatively, the GA known from the patient may also be used to derive estimates for the above biometric parameters, and the degree of agreement between these biometric parameters is used to calculate the biometric similarity index.

According to a useful embodiment, the coefficients of the fitted curve or geometrical shape from the live image are compared to the coefficients of a corresponding geometrical shape or curve fitted to the reference image, and a geometric similarity index is calculated based on this comparison. For example, if an ellipse is fitted to the amniotic sack or the head of the foetus, the differences in the major and minor axis will be calculated, and preferably translated into a score which may be again between 0 (great differences) and 1 (no differences). How to calculate such score for each curve or geometrical shape is pre-determined for each curve or shape and the respective anatomical structure to which it is fitted.

According to an embodiment, the pre-determined curve of geometrical shape fitted to the anatomical structure is or includes an axis of the anatomical structure to be analyzed, in particular the axis of the foetus. Such axis fitted to the live image may thus be compared to an axis fitted to the anatomical structure, in particular the foetus on the reference image. The axis is an important parameter since it will indicate to the operator the position of the baby, such as, for example, the relationship of the presenting part of the maternal pelvis, such as cephalic presentation, breech presentation or shoulder presentation, or the relationship between the longitudinal axis of the foetus and the mother, e.g. longitudinal, oblique or transverse. A comparison of the axis fitted to the live image and the axis fitted to the reference image may be used to calculate an axis similarity index, which will aid the operator in selecting the optimal image. Alternatively, the comparison between the two axes may be used to rotate the images to be compared, preferably the reference image, so that the relative axes are in accordance with one another. Thus, once the axis has been determined on one of the live images and compared to the axis of the reference image, the reference image may be rotated so that its axis is parallel to the axis of the foetus actually observed in the live images. This is helpful particularly in the early stages of pregnancy, where the foetus can move freely in the amniotic sack, and its position and orientation may be highly variably between different ultrasound scans.

In further embodiments, the length of the axis fitted to the anatomical structure on the live image may be used for determining a suitable biometric parameter, which may be used for comparison with the corresponding biometric parameter derived from the physical examination and/or the patient's medical history. For example, the subject's known gestational age, BMI, weight and/or symphysiofundal height or abdominal girth may be used to estimate a foetal actual length, and such length is the biometric parameter to be compared, wherein the degree of agreement is used to calculate the biometric similarity index.

According to a useful embodiment, the method includes a step of displaying the fitted curve or geometrical shape or axis, which has been fitted to the ultrasound image, in particular the live image, overlaid on the ultrasound image, and optionally providing an operator with the opportunity to correct a fitted curve or geometrical shape or axis. In useful embodiments, the points spanning the fitted curve or geometrical shape are overlaid with cursors, which may be manually moved by the operator in order to correct the automatically fitted curve or geometrical shape. For example, if a circle or ellipse is fitted to a foetal head, such circle or ellipse will be displayed as a line overlaid on the ultrasound image, with a number of points (e.g. 2-4 points) highlighted with cursors. The operator may then use a cursor positioning device such as a mouse, a trackball, or a touchpad to be touched by the operator's finger, for moving one of the indicated cursors to a position which corresponds more closely to the anatomical structure as visible on the ultrasound image. Since such displaying of the fitted curve or geometrical shape is preferably done on live images, the operator may temporarily freeze the live image in order to provide time for him to correct the fitted curve or geometrical shape. In useful embodiments, the fitting algorithm is such that such correction is not often necessary. Therefore, the fitted curve or geometrical shape is fitted in real-time to each or at least many of the live images, and the live image is displayed to the operator along with the fitted curve or geometrical shape so that the operator may continually control the quality of the fit, and only occasionally has to enter a manual correction.

In a preferred embodiment, the various similarity indices, i.e. at least two of the image similarity index, biometric similarity index, geometric similarity index and axis similarity index are combined to give an overall matching index. For example, the various similarity indices are added by a weighted addition, the weighting factors being pre-determined. Alternatively, the matching index may be either one of the similarity indices, where such similarity index is above a certain threshold. In addition, or alternatively, the matching index may be the biometric similarity index, if such index is above a certain threshold, and if not may be determined by a weighted addition of the other similarity indices, for example it may then be determined by a weighted addition of the image similarity index and the geometric similarity index.

According to a useful embodiment, the number of ultrasound images corresponds to a series of live images acquired continuously by an operator, wherein at least one of the matching index, the biometric similarity index, the image similarity index, the geometric similarity index and the axis similarity index is calculated in real-time for at least some of the live images directly after they have been acquired. In order to guide the user towards the image with the best similarity indices, a graphic or phonetic signal corresponding to one of the matching index or the similarity indices is issued to the operator for at least some of the live images directly after their acquisition. In an embodiment, the method uses a user-interface such as a display, wherein the live images and the reference image are presented alongside a graphical representation of at least one of the above-identified indices. For example, the matching index or a similarity index may be displayed in a false color scale, wherein for example red indicates a low degree of similarity, and green a high degree of similarity. It is possible to show only the matching index, which is a combination of the similarity indices, so that the user has a simple means of orientation. Alternatively, two or more indices may be separately displayed. For example, in a useful embodiment, both the biometric similarity index and the image similarity index are displayed separately. Thereby, the operator may simultaneously check if the images are similar as such (through the image similarity index), and whether the image content corresponds to the results of the physical examination or medical history (through the biometric similarity index).

According to a useful embodiment, the reference image will be displayed to the user while performing the ultrasound examination. In a further useful embodiment, the display will show instructions on how to perform the scan, and possibly also a video clip demonstrating how to perform the scan.

Alternatively, or additionally, the matching index or one or more of the similarity indices may be issued to the operator as an acoustic or phonetic signal. For example, a beep or phonetic signal may be emitted once the matching index or one or several of the similarity indices (in particular the image similarity index) has reached a value above a pre-determined threshold. Such phonetic signal may thus indicate to the user that this part of the scan is completed and an ultrasound image has been acquired which can be used for analyzing the anatomical structure.

According to a further aspect of the invention, there is provided a computer program comprising program code instructions which, when executed by a processor, enable the processor to carry out the inventive method. The processor may be any machine-based calculating device, in particular it may be part of a computer, such as a pc, server, portable device such as a laptop, hand-held device such as a mobile phone, smartphone, tablet computer etc. The processor may also be part of a remote computer such as a cloud computer or remote server. The processor may be embodied in a CPU or other calculation unit. Such processor may be part of an ultrasound imaging device, in particular a mobile US device such as the Philips Lumify®. Alternatively, the number of ultrasound images may be transferred to a processor which is not part of the ultrasound imaging device, that may be operatively coupled to the ultrasound imaging device. Still alternatively, it is possible to perform the method offline from the ultrasound imaging device, wherein the operator simply performs the ultrasound examination without any immediate feedback, the number of ultrasound images thus acquired are analyzed according to the inventive method, and the offline processor returns either the respective biometric similarity index, image similarity index or matching index for each acquired ultrasound image acquired through the user, so that the user may select the optimal image, or the processor already preforms the selection and returns or indicates to the operator one ultrasound image as best suited to analyze the anatomical structure. Thereby, the operator is retrospectively provided with the best ultrasound image from his or her scan.

According to a further aspect, the invention is related to a computer-readable medium comprising a computer program as disclosed herein. Such computer-readable medium may be any medium able to store digital data, e.g. an optical disc, magnetic disc, solid state, SD-card, etc. The computer-readable medium may also be a cloud or a remote server.

According to another aspect, the invention is related to a biometric similarity index as calculated by the steps of:
  providing an ultrasound image acquired during an ultrasound examination (76) of a subject;
  providing at least one biometric parameter related to an anatomical structure (35), the biometric parameter being derived from a physical examination (70) of the subject, and/or from the subject's medical history;
  determining (100) a biometric parameter from the ultrasound image, and calculating a biometric similarity index, which is a measure of the agreement between the biometric parameter, as determined from the ultrasound image, and the corresponding biometric parameter as derived from the physical examination (70) and/or the subject's medical history.

The biometric similarity index may be calculated and used as described herein, in particular in relation to the inventive method and system. The biometric similarity index may be calculated remotely and provided over a network to the operator, for any ultrasound image sent to the remote server together with the biometric parameter derived from a physical examination of the subject, and/or the subject's medical history.

According to a further aspect, the invention provides a system configured to assist an operator of an ultrasound system in obtaining an ultrasound image well-suited to analyze a pre-determined anatomical structure of a subject. The system may comprise a computer-readable medium comprising a computer program as described above.

Alternatively or additionally, the system may comprise a processor preferably configured for performing the inventive method. The system preferably comprises an ultrasound system, e.g. an ultrasound imaging device, which may be as known in the art. Thus, it comprises an ultrasound probe to be handled by the operator and is configured for acquiring a series of live images from the subject. Further, the ultrasound (US) system preferably comprises a user interface, including a display device, which is configured for displaying the acquired ultrasound images in real time, i.e. each image is displayed directly after it has been acquired from the subject.

In a preferred embodiment, the processor is configured for:
  receiving a number of ultrasound images acquired during an ultrasound examination of the subject;
  receiving at least one biometric parameter related to the anatomical structure derived from a physical examination of the subject and/or the subject's medical history;
  retrieving a reference image from a database, the reference image showing a target view of the anatomical structure;
  for each of the number of ultrasound images, calculating an image similarity index between the ultrasound image and the reference image,
  for at least the ultrasound image(s) having an image similarity index above a certain threshold, or having the best image similarity index, determining a biometric parameter from the ultrasound image, and calculating a biometric similarity index, which is a measure of the agreement between the biometric parameter, as determined from the ultrasound image, and the corresponding biometric parameter as derived from the physical examination and/or the subject's medical history; and performing at least one of:
- displaying a graphical representation of at least one of the biometric similarity index, the similarity index, or a matching index calculated therefrom; and
- selecting an ultrasound image as being best suited to analyze the anatomical structure based on the biometric similarity index, and optionally on the image similarity index.

In a useful embodiment, the system may be configured for saving at least those live images having a biometric similarity index and/or image similarity index or matching index above a certain threshold.

The biometric similarity index and the image similarity index are preferably calculated by a processor operatively coupled to the ultrasound system, wherein the processor is preferably a processor according to the above aspect of the invention.

In a useful embodiment, the system comprises a display unit for displaying the reference image alongside the live image, as well as a graphical representation of the matching index and/or one or more of the similarity indices. As explained above, such graphic representation is useful in guiding the operator towards the optimal image.

According to a further useful embodiment, the system further comprises an adhesive label for fixing to the body surface of the subject. The adhesive label includes markings indicating positions and/or movement directions and/or angulations of the ultrasound probe, which are configured to give directions to the operator to position the probe in a suitable way in order to obtain an ultrasound image well-suited to analyze the anatomical structure. For example, such adhesive label may help the operator to follow the scanning instructions. In useful embodiments, the adhesive label, also referred to as "sticker" includes markings, such as lines, preferably with arrows, which the operator is to follow with the probe. The adhesive label may also contain instructions on the respective probe angulation at various positions. In obstetric ultrasound, the adhesive label is preferably affixed to the abdomen. The probe is placed perpendicular to the skin surface and traced along the label. This makes the scanning fast and easy to perform, even for an inexperienced operator.

According to a useful embodiment, the adhesive label is made of an acoustic rectifying material, preferably a material which filters out scattered ultrasound rays, but allows ultrasound radiation and echoes that are parallel to the material to go through. This will result in a better US image quality. It may be a material which has similar US propagation properties as the body tissue below.

In a preferred embodiment, the system further comprises a database for storing reference images showing suitable target views of the anatomical structure. According to a preferred embodiment, each stored reference image comprises metadata relating to the anatomical structure contained in the stored reference image, and which metadata preferably comprises the biometric parameters corresponding to the respective reference image. Such biometric parameters may be foetal GA, BMI or weight of the pregnant lady, but also biometric parameters which are directly related to the anatomical structure contained in the reference image, e.g. the coefficients of curves or geometrical shapes fitted thereto, for example the length or orientation of an axis of the geometrical structure, the diameter of a circle or ellipse fitted to the anatomical structure etc. In a preferred embodiment, the processor retrieves the reference image from said database based on user input provided via the user-interface that matches the metadata of the retrieved reference image. For example, after the physical examination of the subject or after reviewing the subject's medical history, the operator will enter biometric parameters derived therefrom, e.g. GA, weight, BMI into the system, and the system will automatically compare such data to the metadata available for each stored reference image. The reference image with the best match will be retrieved and used as reference image to compare with the ultrasound images acquired during the subsequent ultrasound examination.

BRIEF DESCRIPTION OF THE DRAWINGS

The invention shall now be illustrated by means of particular embodiments with reference to the attached drawings, in which.

DETAILED DESCRIPTION OF EMBODIMENTS

Throughout the figures, the same or corresponding features or elements of the various embodiments are designated with the same reference numbers.

Figure 1:
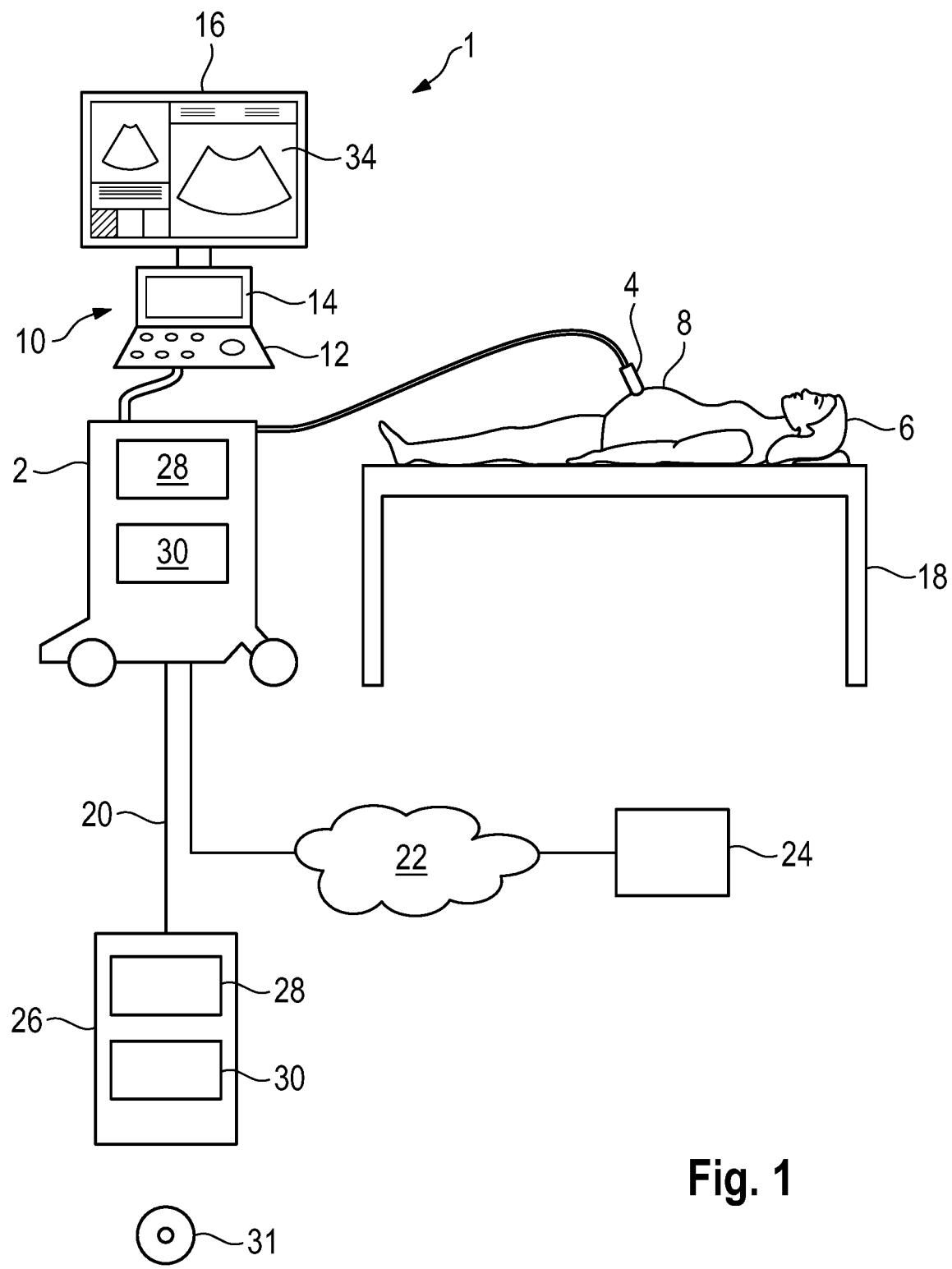
FIG. 1 shows a schematic representation of an ultrasound system according to an embodiment of the invention.

FIG. 1 is a schematic representation of an ultrasound system according to an embodiment of the invention and configured to perform the inventive method. The ultrasound system 1 may include a usual ultrasound hardware unit 2, comprising a CPU 28 and digital storage medium 30, for example a hard disc or solid-state disc. A computer program may be loaded into the hardware unit 2 from CD-ROM 31 or over the internet 22. The hardware unit 2 is connected to a user-interface 10, which comprises a keyboard 12, including a cursor movement device, such as a mouse, trackball etc., and optionally a touchpad 14. The touchpad 14 may act as a cursor movement device and as a display device for displaying imaging parameters. The hardware unit 2 is connected to the ultrasound probe 4, which allows the acquisition of live ultrasound images 34 from a subject or patient 6, lying on a patient bed 18. In the example shown, the probe 4 is held over the patient's abdomen 8. By moving the probe over the abdomen 8 and using various angulations, images may be acquired from the uterus of a pregnant woman 6. The live images 34, acquired with the ultrasound probe, are displayed on screen 16, which may be any commercially available display unit, e.g. a screen, television set, flat screen, projector etc. The operator (not shown) will be holding the probe 4 in his/her hand and thereby control the image acquisition, also by entering commands into the user interface 10. The hardware unit 2, display unit 16 and user interface 10 may also be integrated into a table computer, i.e. the ultrasound system 1 may be a portably US system, such as the Philips Lumify®.

A database 24 of reference images may be included in the hard disc 30, but it is preferably accessible via a remote connection, for example via the internet 22. Thereby, the best available reference images may be provided to a large number of operators, and the reference images may further be more diversified, since for example reference images can be provided for each week (or every second week) of gestational age, as well as for a variety of other diagnostic questions.

The method according to the invention may be performed by CPU 28 of the hardware unit 2 but may also be performed by a processor 28 of a remote computer 26, but which is connected to the ultrasound hardware unit 2 via a data connection 20, which may be a LAN, WIFI or, again, the internet. The inventive method may be executed on a cloud computer 26, and only the result, i.e. the selected ultrasound image or a pointer to the selected image is transferred to the local hardware unit 2. Such remote computer preferably also contains a digital storage medium 30 (such as a hard disc).

Figure 2:
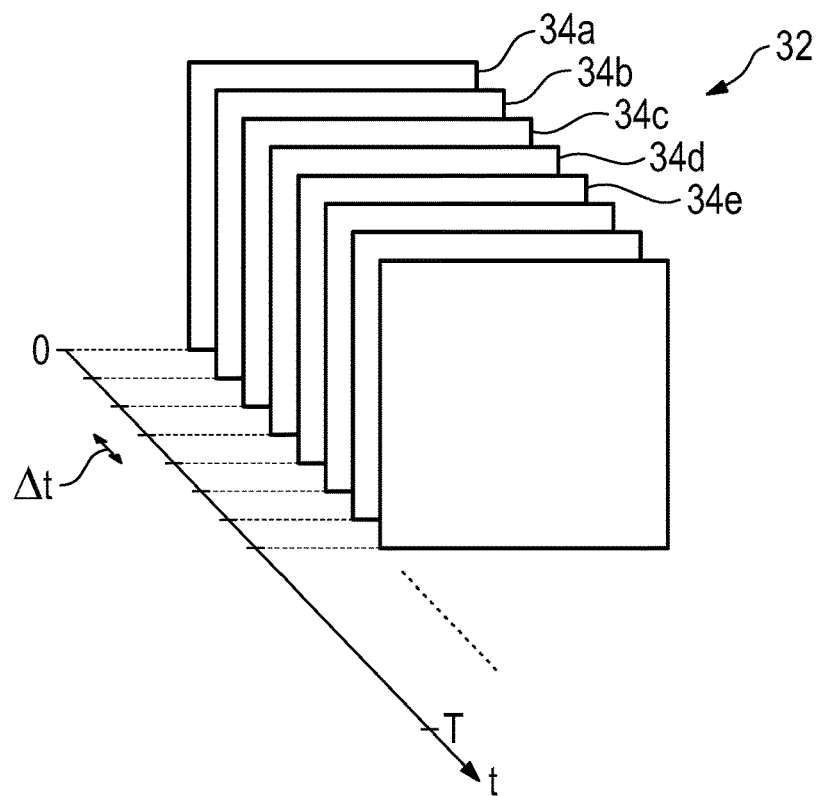
FIG. 2 shows a stack of ultrasound images acquired during an ultrasound examination.

FIG. 2 is a schematic illustration of a number of ultrasound images 32 acquired during an ultrasound scan or examination. Such ultrasound images are usually acquired as a time series of images 34a, 34b, 34c, 34d, as indicated by the timeline in FIG. 2, for example with an image acquisition rate of 10-500 images being acquired per second. Thus, the time Δt between each image might be between 1 and 100 ms, preferably between 5-50 ms. Preferably, the probe position and/or angulation is slowly varied while the images are being acquired, so that each two-dimensional (2D) image 34 captures the ultrasound echoes from a different plane through the subject's body, i.e. has a different field-of-view.

According to the invention, each or at least some of the ultrasound images 34 are compared with a reference images 38, and an image similarity index based on characteristic features in the images is calculated. The degree of matching between the respective live image 34 and the reference image 38 guides the operator to select the right position and/or angulation of the probe.

In addition to such similarity index, the operator may be further guided by the reference image, and by an instructional video clip 56 which shows a video demonstration of an ultrasound scan. For example, the operator scans a foetus as described by the standardized six-step process detailed by the International Society of Ultrasound in Obstetrics and Gynecology. Thus, once the user has selected the desired scan from the six steps, based on the step selected, as well as optionally on biometric parameters obtained from a physical examination of the subject, or from the medical history of the patient, a reference image is retrieved and displayed. Further, an instruction video clip on performing scan is available. As a third step, written instructions for performing the scan can be shown on the display.

Figure 3:
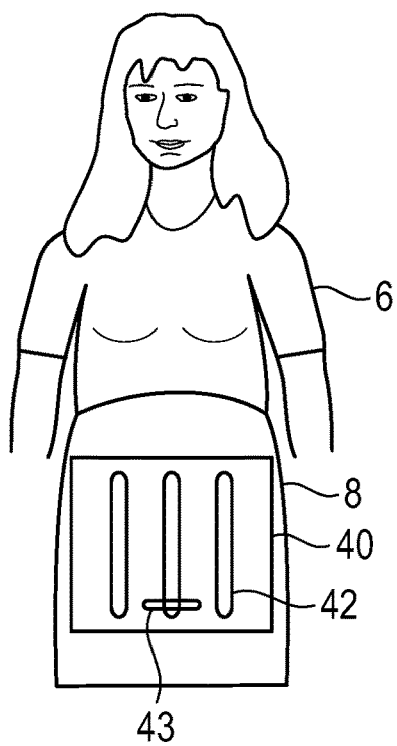
FIG. 3 shows a schematic plan view of a patient with an adhesive label according to an embodiment of the invention.

In addition to these steps, the operator may be guided by an adhesive label 40 made from an acoustic rectifying material and stuck to the abdomen 8 of the pregnant woman 6, as shown in FIG. 3. The adhesive label 40 includes colored, preferably black, longitudinal lines 42, which indicate the direction along which the probe is to be moved. Thus, the operator places the probe perpendicular to the skin surface on the end of one of the lines 42 and traces the probe along the line. The label 40 shown in FIG. 3 also includes a position marker 43, which indicates a position at which the operator is to place the probe, first perpendicular to the skin surface, and then varying the angulation of the probe until the field of view shows the desired anatomical structure. For example, the position marking 43 in FIG. 3 may be used to observe the presentation of the foetus (e.g. cephalic or breech presentation). The longitudinal lines 42 may be traced with the probe in order to determine the number foetuses.

The acoustic rectifying material of the adhesive label 40 enhances the image contrast by absorbing scattered ultrasound rays and also reduces the "acoustic energy dose" to the patient. This makes the scanning fast, easy, and also safe by reducing the acoustic dose.

Figure 4:
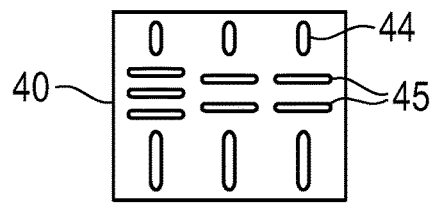
FIG. 4 shows a further embodiment of an adhesive label.

FIG. 4 shows a further example of an adhesive label 40, having lines 44 and position markings 45. The lines 44 and position markers 45 in FIG. 4 may be used to scan the placenta. Thus, the operator will move the probe along lines 44 and stop to vary the respective angulation at the position markers 45.

Figure 5:
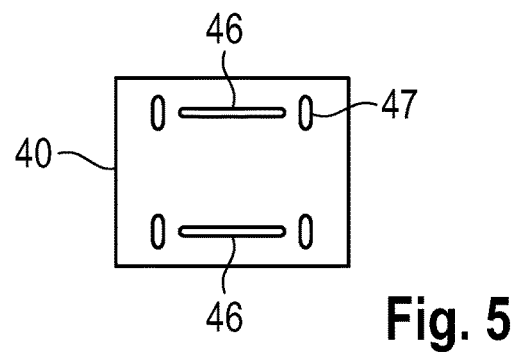
FIG. 5 shows a third embodiment of an adhesive label.

FIG. 5 shows a further embodiment of a respective adhesive label, which may be placed on the abdomen 8 of a pregnant woman in order to gain insight on the amount of amniotic fluid. Thereby, the operator moves the probe along the transverse lines 46 and stops to vary the angulation at position markers 47. A further adhesive label may be provided for indicating the position at which to estimate the foetal heart rate.

All lines 42-46 and markings 43-47 are markings indicating positions or movement directions, which are configured to give directions to the operator to position the probe in a suitable way in order to obtain an ultrasound image well-suited for analysis. In useful embodiments of the invention, the appropriate adhesive label 40 will be selected for the desired scan prior to the ultrasound examination.

Figure 6:
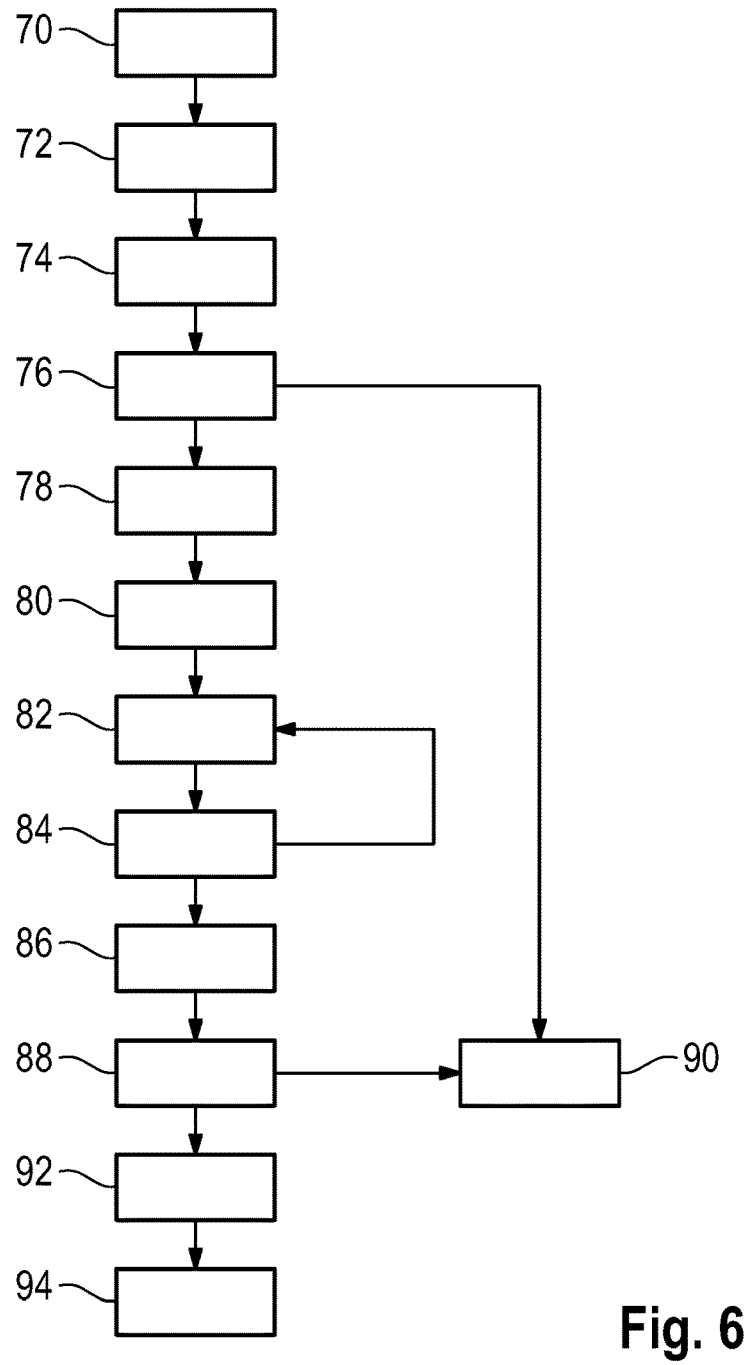
FIG. 6 shows a schematic flow diagram of a workflow performed by an operator when using an embodiment of the invention.

FIG. 6 provides an overview of the protocol which may be used by an operator when using a method or system according to the invention:

In a first step 70, biometric parameters relevant to the anatomical structure to be scanned are obtained from the subject by means of physical examination and/or from the subject's medical history, including by questioning the patient. Such biometric parameter may for example be the subject's weight, height, age, BMI or previous illnesses. For obstetric ultrasound, such biometric parameters derivable from physical examination or medical history include the foetal GA, present and pre-pregnancy weight of the subject, abdominal girth, BMI as well as symphysiofundal height, i.e. the distance from the top of the pubic bone to the top of the pregnant uterus (fundus).

While preparing for the scan, the operator will enter any or all of these biometric parameters into the ultrasound system, for example using the user interface 10, in step 72.

In a useful embodiment, these biometric parameters are used by the ultrasound system 1, in particular by the processor 28, to retrieve an appropriate reference image 38 from the database 24 in step 74.

Before or while the operator begins scanning in step 76, an instructional video clip 56 may be shown to the operator on a video region of the screen 16. The instructional video clip helps the operator to follow the steps to place the probe (ultrasound transducer) at anatomical landmarks and then moving the probe to the desired location.

As soon as live images 34 are acquired in step 76, the processor 28 starts comparing each live image, or at least each of a number of live images acquired at regular intervals, for example every second to tenth live image, with the reference image in step 78. The degree of similarity, i.e. the image similarity index, is calculated in step 80 on the basis of image-related features, preferably without using prior knowledge. The image similarity index is preferably displayed continuously as a number or color, aiding the operator to adjust the position and angle of the probe. In a useful embodiment, the probe is first held perpendicular and traced along the body surface until the image with maximum image similarity index is found. Then, the probe is angulated so that the angle with the maximum image similarity index is identified. Once an image similarity index has been calculated, either for one or several ultrasound images, preferably only for those images having an image similarity index above a certain threshold, a pre-determined geometrical shape or curve is automatically fitted to the anatomical structure visible in the live image 34 in step 80, and such geometrical object 36 is shown overlaid on the live image 34 in step 82.

Figure 8:
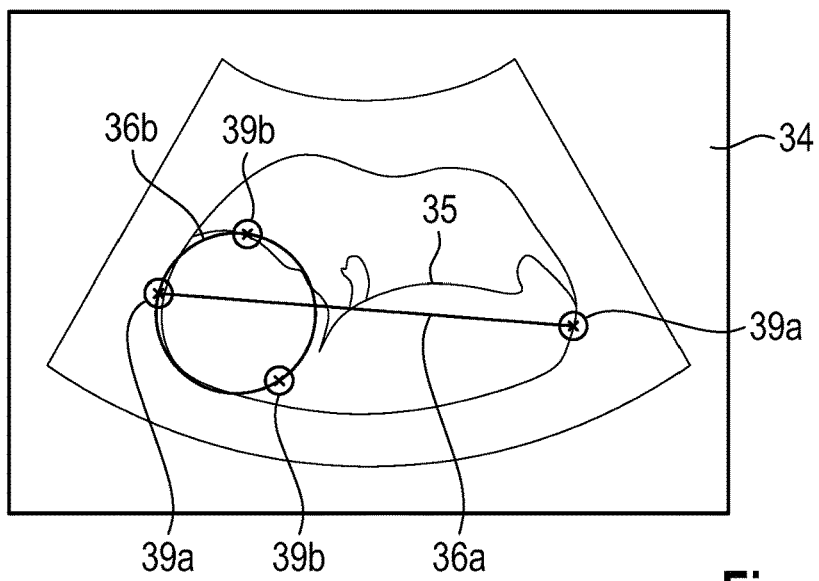
FIG. 8 shown an ultrasound image of a foetus with a display of a geometrical shape.

An example for such overlaid geometrical object 36 is shown in FIG. 8, where the geometrical shapes fitted to the embryo 35 are the axis 36a and the head circumference fitted by a circle 36b. The geometrical shapes or objects 36 are spanned by cursors 39 which define their position, orientation and size. By selecting one of the cursors 39 and dragging it over the display, the user may thus adjust the size, position or orientation of the geometrical shapes 36. For example, the user may select one of the two cursors 39a, defining the two ends of the axis 36a, move the cursor to a different position, and thereby change the length and orientation of the axis 36a. Once such correction has been performed in step 84, the corrected geometrical shape or curve is displayed again in step 82, whereupon naturally a further correction is possible. If no further manual change is made to the fitted geometric shape or curve, the curve coefficients, e.g. the diameter and circumference of the circle 36b, or the length of the axis 36a, may be used for calculating a further similarity index in step 86:

According to one useful embodiment, the coefficients of such fitted geometric shapes are compared in step 86 to the result of a corresponding operation (steps 80 and optional 82 and 84) performed on the reference image. The fitting step may have been performed prior to the scan, it may also have been performed in a different session altogether, and the coefficients of the fitted curve or geometrical shapes are stored as metadata 19 along with the reference image 38. The comparison 86 between such coefficients may be used to compute a further similarity index, the geometrical similarity index, which may be combined with the image similarity index and/or subsequently displayed to the user in step 88.

In addition or alternatively, step 86 comprises the calculation of a biometric parameter from the ultrasound image, and comparing it with a biometric parameter as derived from the physical examination or medical history 72. Such biomedical parameter may be directly related to the coefficients of fitted curves or geometrical shapes, such as the length of the axis or head circumference, or it may be calculated therefrom, such as the foetal weight. As described in detail above, such foetal weight estimates from ultrasound may be compared to the foetal weight derived from symphysiofundal height. The comparison of these data will result in a biometric similarity index, which again may be displayed in step 88, in order to guide the user towards the best probe position and angulation. Alternatively, the biometric similarity index may be used as a reconfirmation of the optimal image as determined by the image similarity index in step 78. Optionally, in step 90, the live images are stored, preferably locally, on the hard disc 30 of the hardware unit 2, and optionally the method starting from step 76 (scanning) is repeated for one or several further ultrasound images. In step 92, one ultrasound image is selected as best suited to analyze the anatomical structure, such as the foetus. This may be done automatically, i.e. the similarity indices calculated for the number of ultrasound images 32 are stored together with the respective image 34 in step 90, and the ultrasound image having the best index is selected. The index may be the biometric similarity index, or any of the other similarity indices. Most preferred, the image having the best matching index is selected, wherein the matching index is calculated on the basis of at least one of the similarity indices. In another embodiment, the user selects the optimal image while he or she is doing the scan, i.e. he watches the graphical presentation of the one or several similarity or matching indices in step 88, and once the graphical representation indicates that the right position and angulation of the probe has been reached, the operator selects that live image (step 92), for example by pressing a button on the user interface 10.

Once the optimal image has been selected in step 92, the image is retrieved from storage 30, and further measurements are made on that image in step 94. For example, the operator then takes further biometry measurements of the foetus on the optimum live image. This measurement on the optimum match produces the best biometric measurements on the foetus and will reduce measurement errors to a minimum.

Figure 7:
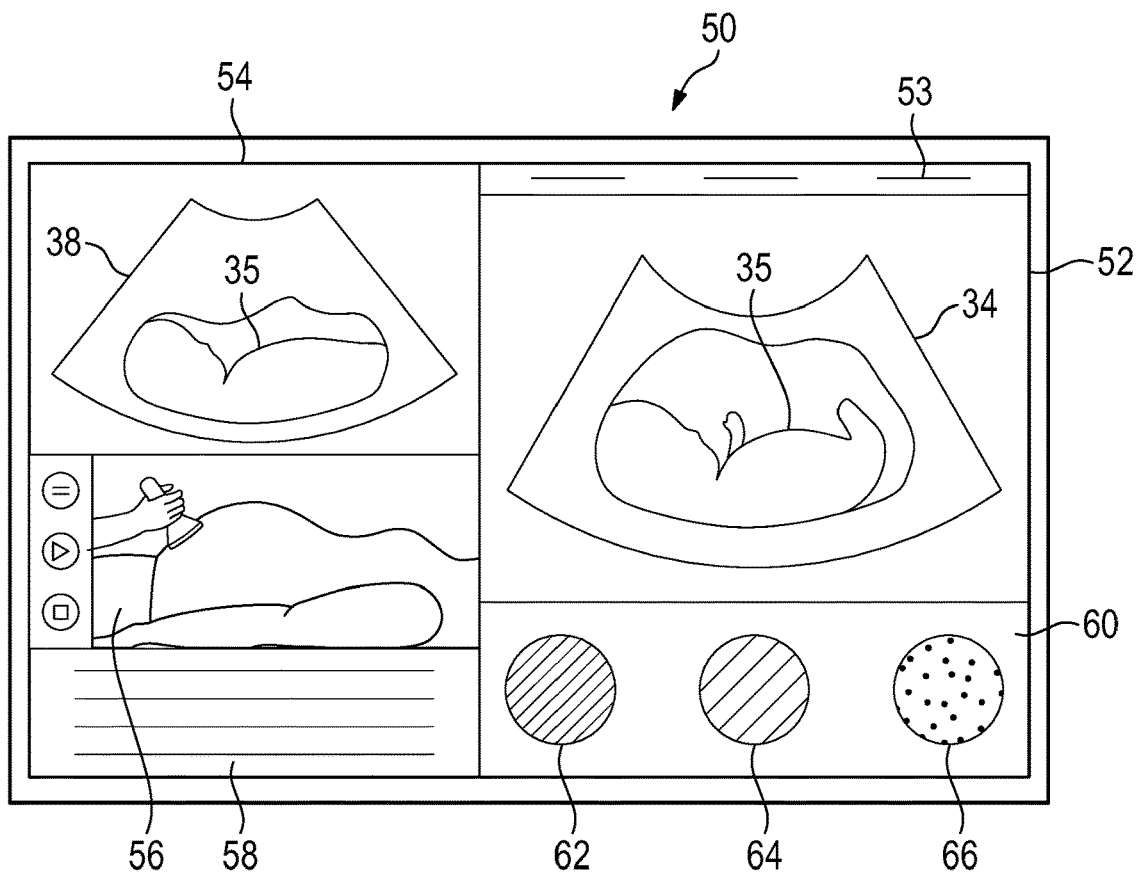
FIG. 7 shows a display shown to the operator of the ultrasound system while performing the inventive method.

FIG. 7 shows an example of the various displays shown to the operator during the scan. In the example of FIG. 7, a single screen 50 (which may be on the display unit 16 of FIG. 1) is used. In other embodiments, only the live image 34 is displayed on the ultrasound system 1 and its display unit 16. The live image 34 in this example shows a foetus 35 as anatomical structure. Information pertaining to the current US examination, such as the name of the patient and possibly the GA, are displayed in header area 53.

Further information, like the reference image 38 for the portion being scanned, may be displayed on another system, which may be an app on a handheld or mobile device, e.g. an app on a mobile ultrasound system like Philips Lumify®, or it could be a separate display device to the main ultrasound system 1. In the example of FIG. 7, the reference image 38, also showing a foetus 35, is displayed in a separate display area 54, which may relate to a separate software app.

In the display area 56, the demonstration video clip 56 is shown to the user. In the display region 58, instructions on how to perform the scan are displayed.

According to an embodiment of the invention, the display 50 contains a further display area 60, which shows graphic indications of one or more similarity index or the matching index. Preferably, these graphical representations 62, 64, 66 display a color according to a false color scale, which is proportional to the respective index. For example, the area 62 may show a color proportional to the image similarity index, area 64 may show a color proportional to the biometric similarity index and area 66 the matching index, which is based on several similarity indices. Alternatively to the color or grey-scale representation of FIG. 7, a numeric may be displayed. Further alternatively, a phonetic signal may be issued.

Figure 9:
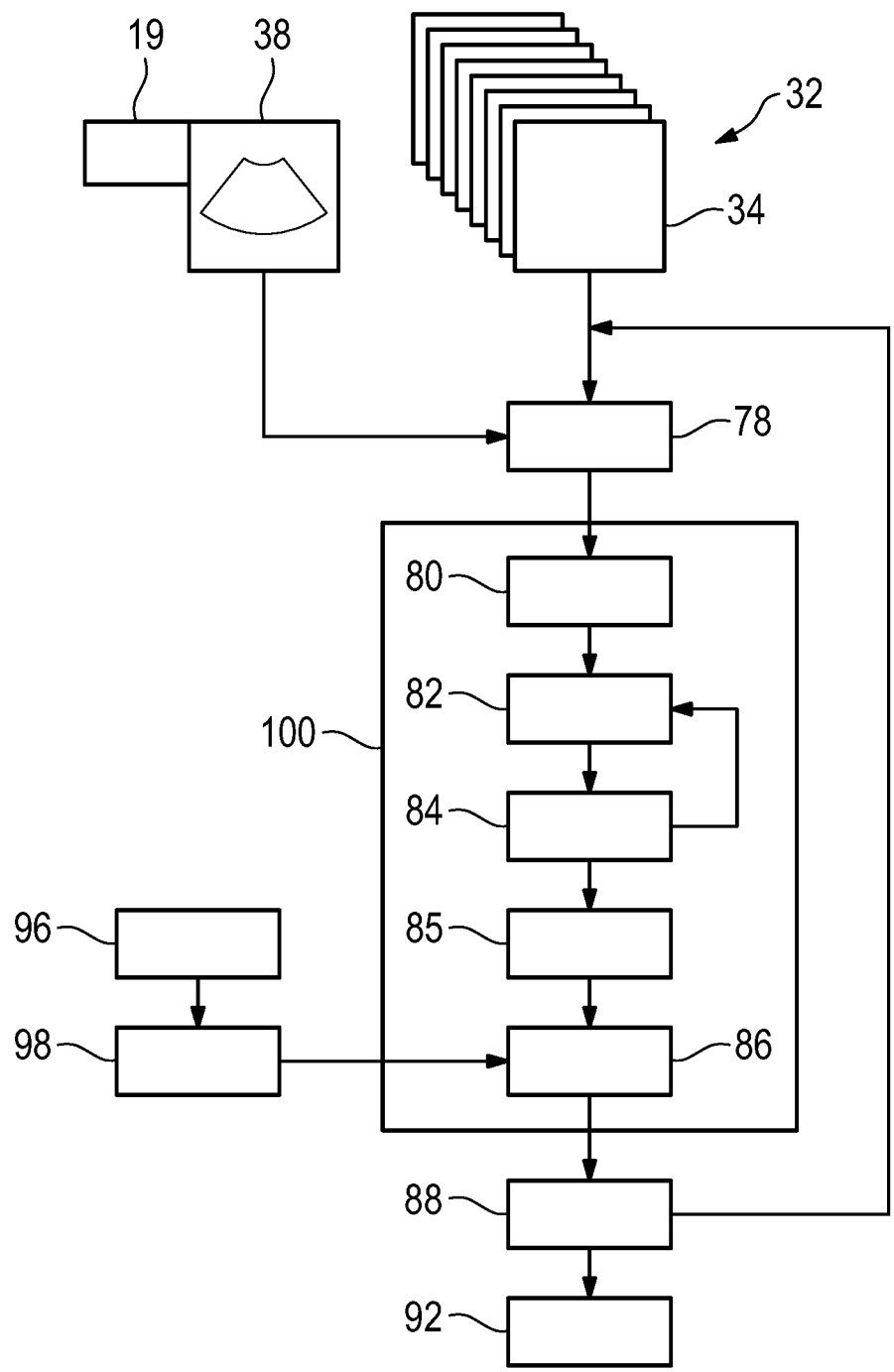
FIG. 9 shows a schematic flow diagram of an embodiment of the inventive method.

The method performed by one of the processors 28 is illustrated in FIG. 9. A number of ultrasound images 34 acquired during an ultrasound examination of the subject is provided, as well as a reference image 38, together with respective metadata 19, which contains biometric and possible further data related to the anatomical structure displayed in the reference image 38. In step 78, an image similarity index is calculated for each image 34, as explained above. The next series of steps 100 concerns the calculation of a biometric similarity index. In the example shown, a suitable curve or geometrical shape 36, which may be used to automatically measure a biometric parameter, is fitted to the respective live image in step 80. Beforehand, the image may be subjected to a suitable pre-processing step, such as a segmentation in order to enhance the visibility of the anatomical structure to which the curve or geometric shape is fitted. The fitted curve or shape is displayed, overlaid on the image 34, in step 82, and the operator reviews the accuracy of the fit in step 84, and if necessary corrects the curve or geometric shape, whereupon the corrected curve or shape is displayed again in step 82. The curve coefficients are extracted in step 85 and are used to derive the respective biometric parameters. For example, a circle or ellipse fitted to the head of a foetus is defined by its diameter, which can easily be used to calculate the circumference of the circle, which is a useful estimate for the biometric parameter HC. Prior to the scan, the operator had entered useful biometric parameters 96 derived from a physical examination or the subject's medical history into the system, and these also are used to derive the same biometric parameter in step 98. In step 86, the biometric parameter calculated from the ultrasound image is compared to the biometric parameter 96 derived from the physical examination, and the measure of agreement is determined as biometric similarity index, which preferably has a value from 0 (no match) to 1 (complete match). In the optional step 88, the biometric and image similarity indices are displayed, whereupon optionally a next image 34 is acquired and processed. Once a sufficient number of images 34 have been processed, the optimal image is selected in step 92.

While the invention has been illustrated and described in detail in the drawings and foregoing description, such illustration and description are to be considered illustrative or exemplary and not descriptive; the invention is not limited to the disclosed embodiments.

REFERENCE SIGNS

1 Ultrasound system
2 Ultrasound hardware
4 Ultrasound probe
6 Patient
8 Abdomen
10 User interface
12 Keyboard/cursor
14 Touchpad
16 Display
18 Patient bed
19 Metadata
20 Data connection
22 Internet
24 Data base of reference images
26 Remote computer
28 CPU
30 Digital storage medium
31 CD-ROM
32 Number of ultrasound images
34 Ultrasound image, live image
35 Anatomical structure, foetus
36 Geometric shapes
38 Reference image
39 Cursors
40 Adhesive label
42, 44, 46 black lines
43, 45, 47 position markers
50 image shown on display
52 display region for live image
53 header area
54 display region for reference image
56 Display region for demonstration video clip
58 Display region for scanning instructions
60 Display region for graphical representations of matching index and similarity indices.
62 graphical representation of image similarity index
64 Graphical indication of matching index
66 Graphical representation of biometric similarity index
70 Physical examination
72 Input of biometric parameters
74 Reference image retrieval and display
76 US image acquisition
78 Calculation of image similarity index
80 Fitting of geometrical shape
82 Display of fitted shape, overlaid on live image
84 Correction of geometrical shape
85 Retrieve coefficients from fitted curve or geometrical shape
86 Comparison of coefficients or biometric parameters
88 Display of similarity indices
90 Save live image
92 Select optimal image
94 Perform further image analysis on optimal image
96 (primary) biometric parameters from physical examination or medical history
98 Calculation of (secondary) biometric parameter(s)
100 Calculation of a biometric similarity index

The invention claimed is:

1. A method of identifying, from a number of ultrasound images acquired during an ultrasound examination of a subject, an ultrasound image best suited to analyze a predetermined anatomical structure of the subject, the method comprising the steps of:

providing a number of ultrasound images acquired during an ultrasound examination of the subject;

providing at least one biometric parameter related to the anatomical structure, the biometric parameter being derived from a physical examination of the subject, and/or from the subject's medical history;

retrieving a reference image from a database, the reference image showing a target view of the anatomical structure;

for each of the number of ultrasound images, calculating an image similarity index between the ultrasound image and the reference image;

for at least the ultrasound image(s) having an image similarity index above a certain threshold, or having the best image similarity index, determining a biometric parameter from the ultrasound image, and calculating a biometric similarity index, which is a measure of the agreement between the biometric parameter, as determined from the ultrasound image, and the corresponding biometric parameter as derived from the physical examination and/or the subject's medical history;

based on the biometric similarity index, and optionally on the image similarity index, selecting an ultrasound image, the selected ultrasound image, as being best suited to analyze the anatomical structure; and for at least the selected ultrasound image, automatically fitting a pre-determined curve or geometrical shape to an anatomical structure shown in the selected ultrasound image, and determining at least a coefficient of the fitted geometrical shape or curve.

2. The method according to claim 1, wherein the reference image is selected from a number of reference images of the anatomical structure, based on at least one biometric parameter derived from the physical examination of the subject, and/or from the subject's medical history.

3. The method according to claim 1, wherein the subject is a pregnant woman, and the anatomical structure is or includes a fetus.

4. The method according to claim 1, wherein the image similarity index between an ultrasound image and the reference image is calculated by one or more of the following steps:
identifying and comparing characteristic features, wherein the characteristic feature are at least one of anatomical features or geometric features, of the ultrasound image and the reference image;
computing and comparing grey level histograms of pixel values of the ultrasound image and the reference image.

5. The method according to claim 1, wherein the biometric similarity index is calculated by automatically or manually taking measurements on the anatomical structure on at least the ultrasound image(s) having an image similarity index above a certain threshold, or having the best image similarity index, and calculating the biometric similarity index therefrom.

6. The method according to claim 1, further comprising a step of calculating the biometric similarity index from the coefficient of the fitted curve or geometrical shape.

7. The method according to claim 1, further comprising the steps of:
comparing the coefficient of the fitted curve or geometrical shape to the coefficient of a corresponding geometrical shape or curve fitted to the reference image, and
calculating a geometric similarity index which is a measure of the agreement between the coefficient derived from the reference image and the coefficient derived from the selected ultrasound image, and/or, if the geometrical shape is an axis, calculating an axis similarity index by comparing the length or orientation of said axis to the length and/or orientation of an axis fitted to the anatomical structure in the reference index,
and wherein the selection of an ultrasound image as being best suited to analyze the anatomical structure is also based on the geometric similarity index and/or the axis similarity index.

8. The method according to claim 1, including, for each selected ultrasound image for which a pre-determined curve or geometrical shape is fitted to an anatomical structure shown in the ultrasound image calculated, the steps of
displaying the fitted curve or geometrical shape or axis overlaid on the selected ultrasound image;
optionally providing an operator with the opportunity to correct the fitted curve or geometrical shape or axis.

9. The method according to claim 7, wherein a matching index between an ultrasound image and the reference image is calculated for at least one of the number of ultrasound images, wherein the matching index is based on the biometric similarity index and one or more of the image similarity index, the geometric similarity index and the axis similarity index.

10. The method according to claim 9, wherein the number of ultrasound images corresponds to a series of live images acquired continuously by an operator, and wherein at least one of the matching index, the biometric similarity index, the image similarity index, the geometric similarity index and the axis similarity index is calculated in real time for at least some of the live images directly after their acquisition, and wherein a graphical or phonetic signal corresponding to one or several of the matching index and the similarity indices is issued to the operator for at least some of the live images directly after their acquisition.

11. A system configured to assist an operator of an ultrasound system in obtaining an ultrasound image well suited to analyze a pre-determined anatomical structure of a subject, the system comprising a processor configured for:
receiving a number of ultrasound images acquired during an ultrasound examination of the subject;
receiving at least one biometric parameter related to the anatomical structure derived from a physical examination of the subject and/or the subject's medical history;
retrieving a reference image from a database, the reference image showing a target view of the anatomical structure;
for each of the number of ultrasound images, calculating an image similarity index between the ultrasound image and the reference image,
for at least the ultrasound image(s) having an image similarity index above a certain threshold, or having the best image similarity index, determining a biometric parameter from the ultrasound image, and calculating a biometric similarity index, which is a measure of the agreement between the biometric parameter, as determined from the ultrasound image, and the corresponding biometric parameter as derived from the physical examination and/or the subject's medical history;
performing at least one of: displaying a graphical representation of at least one of the biometric similarity index, the similarity index, or a matching index calculated therefrom;
and selecting an ultrasound image, the selected ultrasound image, as being best suited to analyze the anatomical structure based on the biometric similarity index, and optionally on the image similarity index; and
for at least the selected ultrasound image, automatically fitting a pre-determined curve or geometrical shape to an anatomical structure shown in the selected ultrasound image, and determining at least a coefficient of the fitted geometrical shape or curve.

12. The system of claim 11, further comprising an ultrasound system comprising an ultrasound probe handled by the operator, and configured for acquiring a series of live images from the subject; and
wherein the processor is operatively coupled to the ultrasound system and configured for receiving the number of ultrasound images from the ultrasound system as a series of live images.

13. The system of claim 12, further comprising an adhesive label for affixing to the body surface of the subject, wherein the adhesive label includes markings indicating positions and/or movement directions and/or angulations of the ultrasound probe, which are configured to give directions to the operator to position the probe in a suitable way in order to obtain an ultrasound image well suited to analyze the anatomical structure.

14. A non-transitory computer-readable medium comprising instructions that when executed on a processor, cause the processor to:

provide at least one biometric parameter related to the anatomical structure, the biometric parameter being derived from a physical examination of the subject, and/or from the subject's medical history;

retrieving a reference image from a database, the reference image showing a target view of the anatomical structure;

for each of the number of ultrasound images, calculating an image similarity index between the ultrasound image and the reference image;

for at least the ultrasound image(s) having an image similarity index above a certain threshold, or having the best image similarity index, determining a biometric parameter from the ultrasound image, and calculating a biometric similarity index, which is a measure of the agreement between the biometric parameter, as determined from the ultrasound image, and the corresponding biometric parameter as derived from the physical examination and/or the subject's medical history;

based on the biometric similarity index, and optionally on the image similarity index, selecting an ultrasound image as being best suited to analyze the anatomical structure;

for at least one of the number of ultrasound images, automatically fitting a pre-determined curve or geometrical shape to an anatomical structure shown in the ultrasound image, and determining at least a coefficient of the fitted geometrical shape or curve.

\* \* \* \* \*